United States Patent [19]

Nedelec et al.

[11] 4,382,942

[45] May 10, 1983

[54] 3-(1,2,5,6-TETRAHYDROPYRIDIN-3-YL)-PHENOLS AND THEIR USE IN PHARMACEUTICAL COMPOSITIONS

[75] Inventors: Lucien Nedelec, Le Raincy; Jacques Guillaume, Le Pre Saint Gervais; Claude Dumont, Nogent sur Marne, all of France

[73] Assignee: Roussel Uclaf, Paris, France

[21] Appl. No.: 328,930

[22] Filed: Dec. 9, 1981

[30] Foreign Application Priority Data

Dec. 15, 1980 [FR] France ................ 80 26540

[51] Int. Cl.³ .................. A61K 31/44; C07D 211/70
[52] U.S. Cl. ................... 424/263; 546/342; 546/343; 546/344
[58] Field of Search ............... 546/344, 342, 343; 424/263

[56] References Cited

U.S. PATENT DOCUMENTS

| 2,498,431 | 2/1950 | Lee | 546/240 |
| 4,046,901 | 9/1977 | Nedelec et al. | 546/240 |
| 4,072,685 | 2/1978 | Nedelec et al. | 546/238 |
| 4,302,462 | 11/1981 | Collins et al. | 546/344 |

*Primary Examiner*—John M. Ford
*Assistant Examiner*—Bernard Dentz

*Attorney, Agent, or Firm*—Hammond & Littell, Weissenberger and Muserlian

[57] ABSTRACT

Novel 3-(1,2,5,6-tetrahydropyridin-3-yl)-phenols of the formula

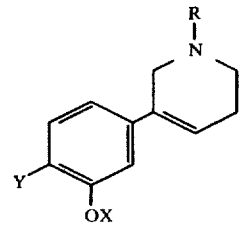

wherein X is selected from the group consisting of hydrogen and an acyl of an organic carboxylic acid of 2 to 7 carbon atoms, Y is selected from the group consisting of hydrogen and —OX, R is selected from the group consisting of hydrogen, alkyl of 1 to 5 carbon atoms optionally substituted with —OH, cycloalkylalkyl of 4 to 7 carbon atoms, alkenyl and alkynyl of 3 to 5 carbon atoms and aralkyl of 7 to 12 carbon atoms optionally substituted on the alkyl with —OH with the proviso that when R is hydrogen, X is hydrogen and their non-toxic, pharmaceutically acceptable acid addition salts having dopaminergic agonist and/or antagonist properties and their preparation.

15 Claims, No Drawings

3-(1,2,5,6-TETRAHYDROPYRIDIN-3-YL)-PHENOLS AND THEIR USE IN PHARMACEUTICAL COMPOSITIONS

STATE OF THE ART

U.S. Pat. No. 2,498,431 describes 2- and 4-hydroxyphenyl-piperidines and French Patent No. 2,401,913 describes 3-(2-hydroxyphenyl)-piperidines substituted on the phenyl with a 4-alkoxy or 4-alkoxyalkyl group. U.S. Pat. Nos. 4,046,901, 4,072,685 and 4,213,989 describes 3-(phenyl)-piperidines substituted with hydroxy or acyloxy.

OBJECTS OF THE INVENTION

It is an object of the invention to provide the novel phenols of formula I and their non-toxic, pharmaceutically acceptable acid addition salts and a novel process and novel intermediates for their preparation.

It is another object of the invention to provide dopaminergic agonist and/or antagonistic compositions and to a novel method of inducing dopaminergic agonist and/or antagonistic activity in warm-blooded animals.

These and other objects and advantages of the invention will become obvious from the following detailed description.

THE INVENTION

The novel compounds of the invention are selected from the group consisting of 3-(1,2,5,6-tetrahydropyridin-3-yl)-phenols of the formula

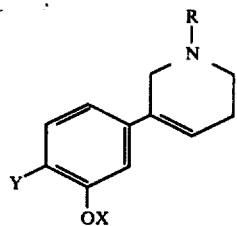

wherein X is selected from the group consisting of hydrogen and an acyl of an organic carboxylic acid of 2 to 7 carbon atoms, Y is selected from the group consisting of hydrogen and —OX, R is selected from the group consisting of hydrogen, alkyl of 1 to 5 carbon atoms optionally substituted with —OH, cycloalkylalkyl of 4 to 7 carbon atoms, alkenyl and alkynyl of 3 to 5 carbon atoms and aralkyl of 7 to 12 carbon atoms optionally substituted on the alkyl with —OH with the proviso that when R is hydrogen, X is hydrogen and their non-toxic, pharmaceutically acceptable acid addition salts.

Examples of X are hydrogen and acyl of an organic carboxylic acid of 2 to 7 carbon atoms such as acetyl, propionyl, n-butyryl, isobutyryl, n-valeryl, pivaloyl and benzoyl. Examples of alkyl of 1 to 5 carbon atoms for R are methyl, ethyl, propyl, isopropyl, butyl, isobutyl and pentyl. Examples of other values for R are cycloalkylalkyl of 4 to 7 carbon atoms such as cyclopropylmethyl; alkenyl of 3 to 5 carbon atoms such as allyl or buten-2-yl; alkynyl of 3 to 5 carbon atoms such as propargyl; and aralkyl of 7 to 12 carbon atoms such as benzyl, phenethyl and phenyl-2-propyl.

Examples of suitable acids for the non-toxic, pharmaceutically acceptable acid addition salts are mineral acids such as hydrochloric acid, hydrobromic acid, nitric acid, sulfuric acid and phosphoric acid and organic acids such as acetic acid, formic acid, propionic acid, benzoic acid, maleic acid, fumaric acid, succinic acid, tartaric acid, citric acid, oxalic acid, glyoxylic acid, aspartic acid, alkane sulfonic acids like methane sulfonic acid and ethane sulfonic acid, arylsulfonic acids like benzene sulfonic and p-toluene sulfonic acids and arylcarboxylic acids.

Among the preferred compounds of formula I and their non-toxic, pharmaceutically acceptable acid addition salts are those wherein R is hydrogen, alkyl of 1 to 5 carbon atoms or aralkyl of 7 to 12 carbon atoms as well as those wherein R is hydrogen or alkyl of 1 to 5 carbon atoms and X is hydrogen. Preferred specific compounds of formula I are 3-(1,2,5,6-tetrahydropyridin-3-yl)-phenol, 3-(1-propyl-1,2,5,6-tetrahydropyridin-3-yl)-phenol and their non-toxic, pharmaceutically acceptable acid addition salts.

The novel process of the invention for the preparation of a compound of formula I and its acid addition salts comprises subjecting a compound of the formula

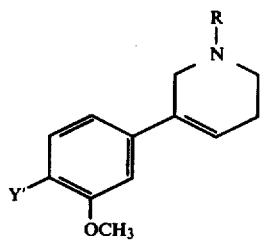

wherein Y' is hydrogen or methoxy and R has the above definition to demethylation to obtain a compound of the formula

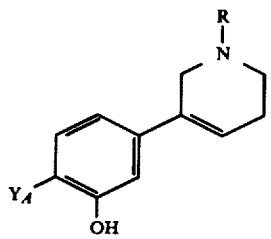

wherein $Y_A$ is selected from the group consisting of hydrogen and —OH and recovering the same and, if desired, salifying it with an acid or subjecting the compound of formula $I_A$ wherein R is other than hydroxy alkyl or aralkyl substituted with an —OH in its salified form to an acylation to form a compound of the formula

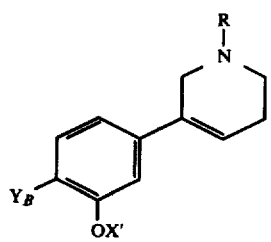

wherein X' is acyl of an organic carboxylic acid of 2 to 7 carbon atoms and $Y_B$ is hydrogen or —OX' and R has the above definition, which may be salified, if desired.

In a preferred mode of the process of the invention, the demethylation of the compound of formula II is effected with hydrobromic acid, pyridinium hydrochloride, lithium thiomethylate or boron tribromide, preferably the latter in methylene chloride when Y' is methoxy. The compound of formula II may be used in the form of the free base or its addition salt. The use of boron tribromide or hydrobromic acid results in the hydrobromide of formula $I_A$ which may be made alkaline with a base to form the free base which may optionally be salified with another acid.

The acylation of the compounds of formula $I_A$ may be effected by reacting the same with a functional acid derivative such as the acid halide, i.e. bromide or chloride or the acid anhydride when R is not hydrogen. When R is hydrogen, it is preferred to use trifluoroacetic acid in the presence of a acid halide. The acylation may optionally be in the presence of solvents such as lower aliphatic ketones, dioxane or dimethylformamide or benzene or toluene at a temperature of 0° to 200° C. The process is preferably effected in the presence of an acid binding agent, especially alkali metal hydroxides or alkali metal carbonates such as potassium carbonate, alkali metal bicarbonates, alkali metal acetates alkaline earth metal carbonates, tertiary amines such as trialkylamines or pyridine or alkali metal alcoholates such as sodium ethylate.

In a modification of the process when R is other than hydrogen, the hydroxy groups are activated by reacting the compound in an inert solvent such as dioxane, dimethylformamide, benzene or toluene with an alkali metal, or alkali metal hydride or alkali metal amide, especially sodium, hydride or sodium amide at a temperature of 0° to 150° C. and then adding the acylation agent to the mixture.

Since the compounds of formula I are basic in nature, they may be reacted with about stoichiometric amounts of a mineral or organic acid to form the corresponding acid addition salts and the base does not have to be isolated.

The starting materials of formula II are novel compounds and are an object of the invention and they may be prepared by reacting a compound of the formula

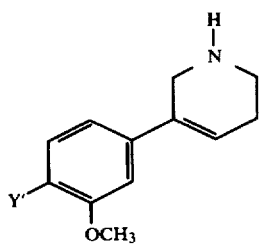

wherein Y' has the above definition with a compound of the formula

R'—Hal    IV wherein R' is R other than hydrogen and Hal may be chlorine, but preferably iodine, to obtain the compound of formula II. The reaction is preferably effected in the presence of an acid binding agent such as alkali metal carbonates like sodium carbonate or potassium carbonate or alkali metal hydroxides or tertiary amines in an inert solvent such as ether, acetone, tetrahydrofuran, dioxane or dimethylformamide.

In preferred embodiments of the latter process, when R in formula II is methyl, an alkyl carbamate, preferably ethyl, is formed on the nitrogen atom and is then reduced. This may be effected by reacting a compound of formula III with an alkyl haloformate in the presence of a base such as an alkali metal carbonate and the resulting carbamate may be reduced with lithium aluminum hydride in refluxing tetrahydrofuran. The methylation may also be effected by reacting a compound of formula III with formal and methanol followed by reduction with sodium borohydride.

To prepare a compound of formula II wherein R is isopropyl, a compound of formula III is reacted with acetone in the presence of a reducing agent such as sodium cyanoborohydride.

The compounds of formula III may be prepared by dehydrating a compound of the formula

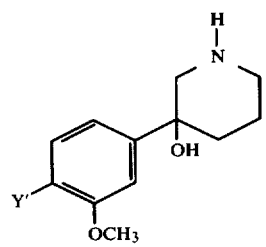

wherein Y' has the above definition such as by refluxing in a strong acid such as hydrochloric acid or by action of phosphoric acid anhydride.

The compounds of formula II wherein R is aralkyl of 7 to 12 carbon atoms substituted on the alkyl with a —OH group may be prepared by reacting a compound of formula III and a suitable halide to obtain a product wherein R represents an aralkyl of 7 to 12 carbon atoms substituted on the alkyl with a keto group and then reducing the ketone group of the product with sodium borohydride, for example.

The compounds of formula V may be prepared by subjecting a compound of the formula

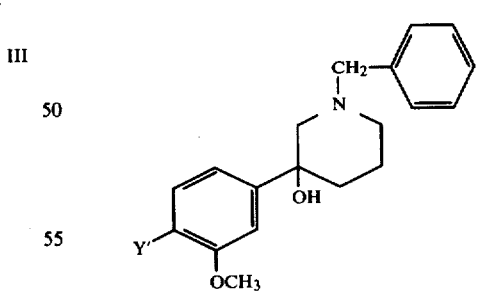

to debenzylation such as by catalytic hydrogenation. The compounds of formula VI are described in French Patent No. 2,310,761, and may be prepared by the process indicated therein.

The novel dopaminergic agonist and/or antagonistic and antiemetic compositions of the invention are comprised of an antiemetically and dopaminergic agonistically and/or antagonistically effective amount of at least one compound of formula I and its non-toxic, pharmaceutically acceptable acid addition salts and an inert pharmaceutical carrier or excipient. The compositions may be in the form of tablets, dragees, gelules, granules, suppositories and injectable solutions or suspensions.

Examples of suitable excipients are talc, arabic gum, lactose, starch, magnesium stearate, cacao butter, aqueous or non-aqueous vehicles, fatty bodies of animal or vegetable origin, paraffinic derivatives, glycols, diverse wetting agents, dispersants or emulsifiers and preservatives.

Among the preferred compositions of the invention are those wherein R is hydrogen, alkyl of 1 to 5 carbon atoms or aralkyl of 7 to 12 carbon atoms as well as those wherein R is hydrogen or alkyl of 1 to 5 carbon atoms and X is hydrogen. Preferred specific compounds of formula I are 3-(1,2,5,6-tetrahydropyridin-3-yl)-phenol, 3-(1-propyl-1,2,5,6-tetrahydropyridin-3-yl)-phenol and their non-toxic, pharmaceutically acceptable acid addition salts.

The compositions possess dopaminergic agonist and/or antagonistic activity as well as an antiemetic activity. For example, the compound of Example 2 possesses predominantly an agonist activity, the compound of Example 4 possesses predominantly dopaminergic antagonistic activity and the compound of Example 6 possesses both dopaminergic agonist and antagonistic activities.

The compositions are useful for the treatment of syndromes of extrapyramidal origin, for the treatment of Parkinson disease and for the treatment of post-encephalitic parkinsonian syndromes, treatment of psychic troubles, behavior problems, character troubles as well as for the treatment of vomitting and nausea of all origins.

The novel method of the invention of inducing dopaminergic agonist and/or antagonistic activity and antiemetic activity in warm-blooded animals, including humans, comprises administering to warm-blooded animals an antiemetically and dopaminergic agonistically and/or antagonistically effective amount of at least one compound of formula I and their non-toxic, pharmaceutically acceptable acid addition salts. The compounds may be administered orally, rectally or parenterally. The usual useful daily dose varies depending on the specific compound and method of administration. For example, the compound of Example 4 may be orally administered at a daily dose of 0.1 to 4 mg/kg, in the human.

In the following examples there are described several preferred embodiments to illustrate the invention. However, it should be understood that the invention is not intended to be limited to the specific embodiments.

EXAMPLE 1

4-(1,2,5,6-tetrahydropyridin-3-yl)-benzene-1,2-diol hydrobromide

STEP A:
3-(3,4-dimethoxyphenyl)-3-hydroxy-piperidine

A mixture of 5 g of 10% palladized carbon and a solution of 9.8 g of N-benzyl-3-(3,4-dimethoxyphenyl)-3-hydroxy-piperidine [described in French patent No. 2,310,761] in 100 ml of ethanol was placed in an autoclave and hydrogen was introduced to obtain a pressure of 50 kg/cm². The autoclave was sealed and was heated at 100° C. and the hydrogen pressure stabilized at 65 kg/cm². The mixture was stirred at 100° C. for 32 hours and was then cooled and filtered. The filtrate was evaporated to dryness under reduced pressure and the residue was chromatographed over silica gel. Elution with a 75-20-5 chloroform-methanol-triethylamine mixture yielded 5.3 g of 3-(3,4-dimethoxyphenyl)-3-hydroxypiperidine.

STEP B:
3-(3,4-dimethoxyphenyl)-1,2,5,6-tetrahydropyridine

A mixture of 8.4 g of the product of Step A and 85 ml of 2 N hydrochloric acid was refluxed under an inert atmosphere for 2 hours and was then evaporated to dryness under reduced pressure. The residue was dissolved in 200 ml of isopropanol and the solution was concentrated to about 100 ml and was iced. The mixture was vacuum filtered and the product was washed with isopropanol, dried at 50° C. under reduced pressure and was crystallized from ethanol to obtain 5.7 g of the hydrochloride of 3-(3,4-dimethoxyphenyl)-1,2,5,6-tetrahydropyridine melting at ≃228° C.

1 g of the said product was dissolved in 20 ml of water and 0.5 ml of sodium hydroxide solution was added thereto while cooling to 0° C. The mixture was extracted with ether and the ether phase was washed with aqueous saturated sodium chloride solution, dried and evaporated to dryness under reduced pressure to obtain 860 mg of 3-(3,4-dimethoxyphenyl)-1,2,5,6-tetrahydropyridine.

STEP C:
4-(1,2,5,6-tetrahydropyridin-3-yl)-benzene-1,2-diol hydrobromide

A solution of 860 mg of the product of Step B in 10 ml of methylene chloride was cooled to 0° to 5° C. and gaseous hydrogen bromide was bubbled therethrough until the pH was acidic. Argon was bubbled through the mixture to remove excess hydrogen bromide and a solution of 0.75 ml of boron tribromide in 10 ml of methylene chloride was added thereto dropwise over 15 minutes at 0° to 5° C. The mixture was stirred at 0° C. for 2 hours and then 10 ml of 95% ethanol were added dropwise thereto. The mixture was evaporated to dryness under reduced pressure and the residue was dissolved in 6 ml of refluxing ethanol. The mixture was cooled and crystallization was induced. The mixture was iced for 16 hours and was vacuum filtered. The product was rinsed with ethanol and dried under reduced pressure to obtain 472 mg of 4-(1,2,5,6-tetrahydropyridin-3-yl)-benzene-1,2-diol hydrobromide melting at ≃196° C.

Analysis: $C_{11}H_{14}BrNO_2$; molecular weight = 272.144. Calculated: %C, 48.55; %H, 5.18; %Br, 29.36; %N, 5.15. Found: %C, 48.6; %H, 5.4; %Br, 29.1; %N, 5.1.

EXAMPLE 2

4-(1-propyl-1,2,5,6-tetrahydropyridin-3-yl)-benzene-1,2-diol hydrobromide

STEP A:
1-propyl-3-(3,4-dimethoxyphenyl)-1,2,5,6-tetrahydropyridine 12.4 g of sodium carbonate and 4 ml of propyl iodide were added under an inert atmosphere to a mixture of 10 g of the hydrochloride of Step B of Example 1 in 100 ml of dimethylformamide and the mixture was stirred for 16 hours and was then poured into 500 ml of iced water. The mixture was extracted with ethyl acetate and the organic phase was washed with aqueous saturated sodium chloride solution, was dried and evaporated to dryness under reduced pressure. The residue was chromatographed over silica gel and was eluted with a 8-1-1 cyclohexane-chloroform-triethylamine mixture. The product was dissolved in methylene chloride and the solution was filtered and the filtrate was evaporated to dryness under reduced pressure to obtain 9.32 g of product which were dissolved in 93 ml of ethyl acetate. A solution of hydrogen chloride in ethyl acetate was added to the solution until the pH was acidic and the mixture was iced for 3 hours and was vacuum filtered. The product was washed with ethyl acetate and was dried under reduced pressure to obtain 9.8 g of 1-propyl-3-(3,4-dimethoxyphenyl)-1,2,5,6-tetrahydropyridine melting at ≃160° C.

STEP B:
4-(1-propyl-1,2,5,6-tetrahydropyridin-3-yl)-benzene-1,2-diol hydrobromide A solution of 2.4 ml of boron tribromide in 33 ml of methylene chloride was added dropwise over 15 minutes at 0° to 5° C. under an inert atmosphere to a mixture of 6.68 g of the product of Step A in 67 ml of methylene chloride and the mixture was stirred at 0° C. for 7 hours. Then, 1.35 ml of water were added thereto dropwise and the mixture was evaporated to dryness under reduced pressure. The residue was taken up in 30 ml of hot ethanol and the solution was filtered. Crystallization was induced and the filtrate was iced for 16 hours and then vacuum filtered. The product was washed with ethanol and dried under reduced pressure to obtain 3.33 g of 4-(1-propyl-1,2,5,6-tetrahydropyridin-3-yl)-benzene-1,2-diol hydrobromide which melted at 175° C. after crystallization from ethanol.

Analysis: $C_{14}H_{20}BrNO_2$; molecular weight = 314.223. Calculated: %C, 53.51; %H, 6.42; %Br, 25.42; %N, 4.46. Found: %C, 53.6; %H, 6.4; %Br, 25.3; %N, 4.5.

EXAMPLE 3
3-(1,2,5,6-tetrahydropyridin-3-yl)-phenol hydrobromide

STEP A: 3-(3-methoxyphenyl)-1-benzyl-piperidine-3-ol hydrochloride 9 g of magnesium were activated by sublimation of iodine and were cooled and 20 ml of ether and 2 ml of tetrahydrofuran were added thereto. Then, 2 ml of m-bromoanisole were added thereto under an inert atmosphere and the reaction began. Then, a solution of 50 ml of m-bromoanisole in 200 ml of ether and 20 ml of tetrahydrofuran were added dropwise to the mixture over 2 hours and the mixture was refluxed for one hour and allowed to stand for 16 hours. 120 ml of the solution were cooled to 5° to 10° C. while adding a solution of 20 g of N-benzyl-3-piperidone in 100 ml of tetrahydrofuran dropwise under an inert atmosphere. The mixture was stirred for 3 hours and was then cooled in an ice bath. 200 ml of aqueous saturated ammonium chloride solution were added dropwise to the mixture at 5° to 20° C. and the mixture was vacuum filtered. The decanted aqueous phase was extracted with ethyl acetate and the ethyl acetate extract was extracted with 2 N hydrochloric acid. The aqueous extract was made alkaline by addition of sodium hydroxide and was extracted with ethyl acetate. The organic phase was washed with water, dried and evaporated to dryness under reduced pressure. The 30 g of residue were dissolved in ethyl acetate and a solution of hydrogen chloride gas in ethyl acetate was added thereto until the pH was acidic. Crystallization was induced and the mixture was vacuum filtered to obtain 3-(3-methoxyphenyl)-1-benzyl-piperidine-3-ol hydrochloride melting at 210° C.

STEP B:
1-benzyl-3-(3-methoxyphenyl)-1,2,5,6-tetrahydropyridine

A mixture of 3.25 g of the product of Step A and 65 ml of xylene was heated to 140° C. with stirring and after the addition of 2 g of phosphoric acid anhydride, the mixture was stirred at 140° C. for 2 hours and was then iced. Ice was then added to the mixture with caution and was diluted with water and ethyl acetate. The mixture was made alkaline by addition of triethylamine and was stirred until total dissolution occurred. The mixture was filtered and the decanted aqueous phase was extracted with ethyl acetate. The organic extract was washed with aqueous saturated sodium chloride solution, dried and evaporated to dryness under reduced pressure. The residue was chromatographed over silica gel and was eluted with a 9-1 cyclohexane-ethyl acetate mixture to obtain 1.97 g of 1-benzyl-3-(3-methoxyphenyl)-1,2,5,6-tetrahydropyridine.

STEP C: Ethyl 3-(3-methoxyphenyl)-1,2,5,6-tetrahydro-1-pyridine-carboxylate

A solution of 11.4 g of the product of Step B, 25 ml of benzene and 5.9 ml of ethyl chloroformate was refluxed for 3 hours and was then evaporated to dryness under reduced pressure. Excess ethyl chloroformate was entrained with benzene to obtain 11 g of ethyl 3-(3-methoxyphenyl)-1,2,5,6-tetrahydro-1-pyridine-carboxylate.

STEP D:
3-(3-methoxyphenyl)-1,2,5,6-tetrahydropyridine hydrochloride

A solution of 11 g of the product of Step C in 110 ml of n-butanol and 11 g of potassium hydroxide was heated for 6 hours at 120° C. and the mixture was cooled and diluted with water. The mixture was extracted with ethyl acetate and the organic phase was washed with aqueous saturated sodium chloride solution, dried and evaporated to dryness under reduced pressure. The residue was chromatographed over silica gel and was eluted with a 6-3-1 chloroform-acetone-triethylamine mixture. The distilled fraction residue was taken up in methylene chloride and the solution was filtered and evaporated to dryness under reduced pressure to obtain 8 g of 3-(3-methoxyphenyl)-1,2,5,6-tetrahydropyridine.

7.7 g of the said product were dissolved in 30 ml of ethyl acetate and the pH of the solution was made acidic by addition of a solution of hydrogen chloride in ethyl acetate. Crystallization was induced and the mixture was iced for 2 hours and was vacuum filtered. The product was washed with ethyl acetate and dried under reduced pressure. The product was crystallized from isopropanol to obtain 6.5 g of 3-(3-methoxyphenyl)-1,2,5,6-tetrahydropyridine hydrochloride melting at 202° C.

STEP E: 3-(1,2,5,6-tetrahydropyridin-3-yl)-phenol hydrobromide

A mixture of 11.25 g of the product of Step D in 112 ml of 66% hydrobromic acid was heated at 70° C. with stirring under an inert atmosphere for 2 hours and was then distilled to dryness under reduced pressure. The residue was dissolved in 150 ml of isopropanol and 50 ml of isopropanol were distilled off. The mixture was cooled and crystallization was induced. The mixture was iced for 16 hours and was vacuum filtered. The product was washed with isopropanol and dried under reduced pressure at 50° C. to obtain 5.4 g of product which were dissolved in 200 ml of refluxing isopropanol. The solution was concentrated to 100 ml and crystallization was started. Filtration of the mixture yielded 4.97 g of 3-(1,2,5,6-tetrahydropyridin-3-yl)-phenol hydrobromide melting at ≃212° C.

Analysis: $C_{11}H_{14}BrNO$; melting weight=256.144. Calculated: %C, 51.58; %H, 5.51; %Br, 31.19; %N, 5.47. Found: %C, 51.6; %H, 5.4; %Br, 31.0; %N, 5.4.

EXAMPLE 4

3-(1-propyl-1,2,5,6-tetrahydropyridin-3-yl)-phenol hydrochloride

STEP A:

3-(3-methoxyphenyl)-1-propyl-1,2,5,6-tetrahydropyridine

A mixture of a solution of 5 g of the product of Step D of Example 3 in 50 ml of dimethylformamide, 7 g of sodium carbonate and 2.3 ml of n-propyl iodide was stirred for 16 hours under an inert atmosphere and was then poured into 250 ml of iced water. The mixture was extracted with ethyl acetate and the organic phase was washed with aqueous saturated sodium chloride solution, dried and evaporated to dryness under reduced pressure. The residue was chromatographed over silica gel and was eluted with an 8-1-1 cyclohexane-chloroform-triethylamine mixture. The eluate was distilled to dryness under reduced pressure to obtain 4.84 g of 3-(3-methoxyphenyl)-1-propyl-1,2,5,6-tetrahydropyridine.

STEP B:

3-(1-propyl-1,2,5,6-tetrahydropyridin-3-yl)-phenol hydrochloride

A mixture of 3.9 g of the product of Step A and 7.8 g of pyridinium hydrobromide was stirred under an inert atmosphere for 2 hours at 200° C. and was then cooled and taken up in water. The mixture was stirred until dissolution and was made alkaline by addition of ammonium hydroxide. The mixture was extracted with methylene chloride and the organic phase was washed with aqueous saturated sodium chloride solution, dried and evaporated to dryness under reduced pressure. The residue was chromatographed over silica gel and was eluted with a 95-5 chloroform-methanol mixture. The solution was distilled to dryness under reduced pressure and the residue was taken up in methylene chloride. The solution was filtered and evaporated to dryness under reduced pressure to obtain 3.13 g of 3-(1-propyl-1,2,5,6-tetrahydropyridin-3-yl)-phenol.

A solution of hydrogen chloride in ethyl acetate was added to a solution of 6.5 g of the said product in 32.5 ml of ethyl acetate until the pH was 4 and crystallization was started. The mixture was iced for 16 hours and was vacuum filtered. The product was washed with ethyl acetate, dried under reduced pressure and crystallizated from isopropanol to obtain 5 g of 3-(1-propyl-1,2,5,6-tetrahydropyridin-3-yl)-phenol hydrochloride melting at ≃205° C.

Analysis: $C_{14}H_{20}ClNO$: molecular weight=253.775. Calculated: %C, 66.26; %H, 7.94; %Cl, 13.97; %N, 5.52. Found: %C, 66.2; %H, 7.9; %Cl, 14.1; %N, 5.5.

EXAMPLE 5

3-(1-phenethyl-1,2,5,6-tetrahydropyridin-3-yl)-phenol fumarate

STEP A:

3-(3-methoxyphenyl)-1-phenethyl-1,2,5,6-tetrahydropyridine

A mixture of 5 g of 3-(3-methoxyphenyl)-1,2,5,6-tetrahydropyridine hydrochloride, 100 ml of acetone, 7 g of sodium carbonate and 3.5 ml of phenethyl bromide was refluxed for 16 hours and was filtered. The filtrate was evaporated to dryness and the residue was chromatographed over silica gel. The elution with a 7-3 cyclohexane-ethyl acetate mixture yielded 6.2 g of 3-(3-methoxyphenyl)-1-phenethyl-1,2,5,6-tetrahydropyridine.

STEP B:

3-(1-phenethyl-1,2,5,6-tetrahydropyridin-3-yl)-phenol fumarate

A mixture of 6 g of the product of Step A and 12 g of pyridinium hydrochloride was heated at 200° C. with stirring for 2½ hours and the mixture was cooled and diluted with water. Ammonium hydroxide was added to the mixture which was then extracted with methylene chloride. The organic phase was washed with water, dried and evaporated to dryness. The residue was chromatographed over silica gel and was eluted with an 8-2 chloroform-acetone mixture to obtain 4.9 g of 3-(1-phenethyl-1,2,5,6-tetrahydropyridin-3-yl)-phenol melting at 155° C.

3.5 g of the said product were dissolved in 50 ml of isopropanol and a solution of 1.5 g of fumaric acid in 15 ml of isopropanol was added thereto. The mixture was cooled and vacuum filtered and the recovered product was washed with isopropanol and dried to obtain 3.4 g of 3-(1-phenethyl-1,2,5,6-tetrahydropyridin-3-yl)-phenol fumarate melting at 210° C.

Analysis: $C_{23}H_{25}O_5N$; molecular weight=395.458. Calculated: %C, 69.86; %H, 6.37; %N, 3.54. Found: %C, 69.9; %H, 6.5; %N, 3.5.

EXAMPLE 6

3-(1-ethyl-1,2,5,6-tetrahydropyridin-3-yl)-phenol oxalate

STEP A:

3-(3-methoxyphenyl)-1-ethyl-1,2,5,6-tetrahydropyridine 9.8 g of sodium carbonate and 2.6 ml of ethyl iodide were added to a suspension of 7 g of 3-(3-methoxyphenyl)-1,2,5,6-tetrahydropyridine hydrochloride and 70 ml of dimethylformamide and the mixture was stirred for 16 hours and was diluted with water. The mixture was extracted with ethyl acetate and the organic extract was washed with water, dried and evaporated to dryness under reduced pressure. The residue was chromatographed over silica gel and was eluted with an 8-1-1 cyclohexane-chloroform-triethylamine mixture to obtain 5.3 g of 3-(3-methoxyphenyl)-1-ethyl-1,2,5,6-tetrahydropyridine.

STEP B:

3-(1-ethyl-1,2,5,6-tetrahydropyridin-3-yl)-phenol oxalate

A mixture of 5.2 g of the product of Step A and 10.4 g of pyridinium hydrochloride was heated at 200° C. for 2½ hours and the mixture was cooled and diluted with water. Ammonium hydroxide was added to the mixture which was then extracted with methylene chloride. The organic phase was washed with water, dried and evaporated to dryness under reduced pressure. The residue was chromatographed over silica gel and was eluted with a 6-3-1 cyclohexane-chloroform-triethylamine mixture to obtain 3.95 g of 3-(1-ethyl-1,2,5,6-tetrahydropyridin-3-yl)-phenol. 3.85 g of the latter were dissolved in 40 ml of isopropanol and 2.4 g of oxalic acid were added thereto. The mixture was cooled and filtered and the product was washed with isopropanol and dried to obtain 3.57 g of 3-(1-ethyl-1,2,5,6-tetrahydropyridin-3-yl)-phenol oxalate melting at 240° C.

Analysis: $C_{14}H_{18}NO_3$; molecular weight=217.31. Calculated: %C, 67.72; %H, 7.31; %N, 5.64. Found: %C, 67.4; %H, 7.3; %N, 5.6.

EXAMPLE 7

3-(1-cyclopropylmethyl-1,2,5,6-tetrahydropyridin-3-yl)-phenol fumarate

STEP A:

1-cyclopropylmethyl-3-(3-methoxyphenyl)-1,2,5,6-tetrahydropyridine

A mixture of 10 g of 3-(3-methoxyphenyl)-1,2,5,6-tetrahydropyridine hydrochloride, 100 ml of dimethylformamide, 14 g of sodium carbonate and 4.4 ml of chloromethyl cyclopropane was heated at 75° C. for 24 hours and was then cooled and diluted with water. The mixture was extracted with ethyl acetate and the organic phase was washed with water, dried and evaporated to dryness under reduced pressure. The residue was chromatographed over silica gel and was eluted with an 8-1-1 cyclohexane-chloroform-triethylamine mixture to obtain 9.25 g of 1-cyclopropylmethyl-3-(3-methoxyphenyl)-1,2,5,6-tetrahydropyridine.

EXAMPLE 8

STEP B:

3-(1-cyclopropylmethyl-1,2,5,6-tetrahydropyridin-3-yl)-phenol fumarate

Using the procedure of Step B of Example 5, 13.35 g of the product of Step A and 27 g of pyridinium hydrochloride were reacted to obtain 10.2 g of 3-(1-cyclopropylmethyl-1,2,5,6-tetrahydropyridin-3-yl)-phenol and 4.5 g of the latter were reacted with fumaric acid to obtain 5.04 g of 3-(1-cyclopropylmethyl-1,2,5,6-tetrahydropyridin-3-yl)-phenol fumarate melting at 210° C.

Analysis: $C_{34}H_{42}N_2O_6$; molecular weight=574.732. Calculated: %C, 71.06; %H, 7.37; %N, 4.87. Found: %C, 71.3; %H, 7.4; %N, 4.9.

EXAMPLE 8

1-[{3-(3-hydroxyphenyl)-1,2,5,6-tetrahydropyridin-1-yl}methyl]benzene methanol fumarate

STEP A:

1-phenyl-2-[3-(3-methoxyphenyl)-1,2,5,6-tetrahydropyridin-1-yl]-ethanone

A mixture of 10 g of 3-(3-methoxyphenyl)-1,2,5,6-tetrahydropyridine hydrochloride, 200 ml of acetone, 14 g of sodium carbonate and 9.3 g of phenacyl bromide were refluxed for 3 hours and was filtered. The filtrate was evaporated to dryness to obtain 14 g of 1-phenyl-2-[3-(3-methoxyphenyl)-1,2,5,6-tetrahydropyridin-1-yl]-ethanone.

STEP B:

1-phenyl-3-(3-methoxyphenyl)-1,2,5,6-tetrahydropyridine-ethanol 2.72 g of sodium borohydride were added to a solution of 14 g of the product of Step A in 135 ml of methanol cooled to 0° C. and the mixture was stirred at 0° C. for 2 hours and was then poured into 500 ml of iced water. The mixture was extracted with ethyl acetate and the organic phase was washed with water, dried and evaporated to dryness under reduced pressure. The residue was chromatographed over silica gel and was eluted with a 7-3-benzene-ethyl acetate mixture to obtain 13.44 g of 1-phenyl-3-(3-methoxyphenyl)-1,2,5,6-tetrahydropyridine-ethanol.

STEP C:

1-[{3-(3-hydroxyphenyl)-1,2,5,6-tetrahydropyridin-1-yl}-methyl]-benzenemethanol fumarate A mixture of 5 g of the product of Step B, 200 ml of dimethylformamide and 4.3 g of lithium thiomethylate was refluxed for 3 hours and the mixture was cooled and poured into iced water. The mixture was extracted with ethyl acetate and the organic phase was washed with water, dried and evaporated to dryness under reduced pressure. The residue was chromatographed over silica gel and was eluted with a 95-5 chloroform-methanol mixture to obtain 5 g of 1-[{3-(3-hydroxyphenyl)-1,2,5,6-tetrahydropyridin-1-yl}-methyl]-benzenemethanol.

5.4 g of the latter were dissolved in 100 ml of hot isopropanol and 2.12 g of fumaric acid were added thereto. The mixture was iced and vacuum filtered and the crystals were washed with isopropanol, dried and crystallized from ethanol to obtain 4.33 g of 1-[{3-(3-hydroxyphenyl)-1,2,5,6-tetrahydropyridin-1-yl}-methyl]-benzenemethanol fumarate melting at 173° C.

Analysis: $C_{21}H_{23}NO_4$; molecular weight=706.844. Calculated: %C 71.37; %H 6.56; %N, 3.96. Found: %C, 71.7; %H, 6.8; %N, 4.0.

EXAMPLE 9

3-(1-allyl-1,2,5,6-tetrahydropyridin-3-yl)-phenol fumarate

STEP A:

1-allyl-3-(3-methoxyphenyl)-1,2,5,6-tetrahydropyridine

A mixture of 7 g of 3-(3-methoxyphenyl)-1,2,5,6-tetrahydropyridine hydrochloride, 100 ml of dimethylformamide, 9.8 g of sodium carbonate and 3.75 g of allyl bromide was stirred for 6 hours and was then filtered. The filtrate was evaporated to dryness and the residue was chromatographed over silica gel. Elution with a 7-3 benzene-ethyl acetate mixture yielded 5.9 g of 1-allyl-3-(3-methoxyphenyl)-1,2,5,6-tetrahydropyridine.

STEP B:

3-(1-allyl-1,2,5,6-tetrahydropyridine-3-yl)-phenol fumarate

Using the procedure of Step C of Example 8, 4.9 g of the product of Step A and 4 g of lithium thiomethylate were reacted to obtain a raw product which was chromatographed over silica gel. The product was eluted with a 6-3-1 cyclohexane-chloroform-triethylamine mixture and was treated with fumaric acid in isopropanol to obtain 5.73 g of 3-(1-allyl-1,2,5,6-tetrahydropyridine-3-yl)-phenol fumarate melting at 168° C.

EXAMPLE 10

Tablets were prepared containing 100 mg of either 3-(1,2,5,6-tetrahydropyridin-3-yl)-phenol hydrobromide or 3-(1-propyl-1,2,5,6-tetrahydropyridin-3-yl)-phenol hydrochloride and sufficient excipient of lactose, starch, talc and magnesium stearate for a final tablet weight of 150 mg.

PHARMACOLOGICAL DATA

A. Antagonism to apomorphine stereotypes

The test was effected on groups of 5 rats by a test inspired by JANSSEN et al [Arzneim. Forsch., Vol. 15 (1965), p. 104–117 and Vol. 17 (1967), p. 841–854] and each rat was placed in a plexiglass box measuring 20×10×10 cm with the bottom being covered with a thin layer of wood curls. A dose of 1.5 mg/kg of apomorphine hydrochloride was intraveinously injected into each rat 30 minutes after the intraperitoneal administration of the test compound. The rats were observed for one minute 15 minutes after the apomorphine injection and the stereotypical movements of oral sphere were evaluated by the Boissier et al method [Therapie, Vol. 25 (1970), p. 933–949]: No characteristic reaction (0), a few sniffles, licking and jaw movements (1), intense sniffles and continuous licking (2) and continuous jaw movement (3). The intensity of the stereotypes was expressed in the form of a score of 0 to 15 based on the sum of the values obtained from 5 rats in each group 15 minutes after the apomorphine injection. The compound of Example 4 antagonisted the stereotypes of apomorphine at a dose of 10 mg/kg.

B. Behavior After Unilateral Injury Of Nigrostriated Fasciculus

The lesion is effected in male rats of about 220 g by unilateral injection into the nigrostriated dopaminergic fasciculus of 8 μg of 6-hydroxydopamine in solution at 2 μg/μl (U. Ungerstedt. Acta Physiol. Scand. 1971, 82 suppl. 367, 69–93).

In such animals the direct dopaminergic agonists such as apomorphine, administered by general route, bring about rotation behavior in the contralateral direction to the injured side.

The products to be tested are administered, by intraperitoneal route, at least five weeks after the lesion. The animals are placed in an automatic rotometer which counted the number of rotations of each animal in two ways.

To evaluate the dopaminergic agonistic activity, the products to be tested are administered and the contralateral rotations thus caused are observed.

To evaluate the dopaminergic antagonistic activity, the products to be tested are administered, then apomorphine, and the reduction in the number of rotations which are caused by the apomorphine is observed. Under these conditions, the product of Example 2 provoked rotations at a dose of 10 mg/kg, the products of Example 4 and 7 antagonized the rotations caused by apomorphine at 10 and 20 mg/kg, respectively and the product of Example 6 possessed both dopaminergic agonist and antagonistic activity at 20 mg/kg.

C. Antiemetic Activity

The antagonism vis-a-vis vomitting provoked by apomorphine was studied in dogs by the method of Chen et al [J. Pharmc. exp. Therap., Vol. 93 (1959), p 245–250]. The number of vomits provoked by a subcutaneous injection of 0.1 mg/kg of apomorphine hydrochloride was determined for each animals 8 days before the test. The test compound in an aqueous solution was administered subcutaneously at varying doses 30 minutes before apomorphine hydrochloride and the products of Examples 2 and 4 antagonised the vomitting provoked by apomorphine.

D. Acute Toxicity

The lethal dose ($DL_O$) was determined for the different products after oral administration to mice. $DL_O$ is the maximum dose producing any mortality at the end of 8 days. The $DL_O$ for products is reported in Table I.

TABLE I

| Compound of Example | $DL_0$ in mg/kg |
|---|---|
| 1 | 200 |
| 2 | >1000 |
| 3 | 400 |
| 4 | 200 |
| 6 | ≧400 |
| 7 | 200 |

Various modifications of the products and processes of the invention may be made without departing from the spirit or scope thereof and it is to be understood that the invention is intended to be limited only as defined in the appended claims.

What we claim is:

1. A compound selected from the group consisting of 3-(1,2,5,6-tetrahydropyridin-3-yl)-phenols of the formula

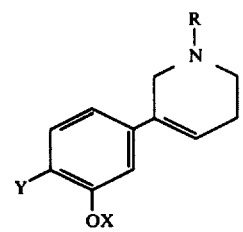

wherein X is selected from the group consisting of hydrogen and an acyl of an organic carboxylic acid of 2 to 7 carbon atoms, Y is selected from the group consisting of hydrogen and —OX, R is selected from the group consisting of hydrogen, alkyl of 1 to 5 carbon atoms optionally substituted with —OH, cycloalkylalkyl of 4 to 7 carbon atoms, alkenyl and alkynyl of 3 to 5 carbon atoms and aralkyl of 7 to 12 carbon atoms optionally substituted on the alkyl with —OH with the proviso that when R is hydrogen, X is hydrogen and their nontoxic, pharmaceutically acceptable acid addition salts.

2. A compound of claim 1 wherein R is selected from the group consisting of hydrogen, alkyl of 1 to 5 carbon atoms and aralkyl of 7 to 12 carbon atoms.

3. A compound of claim 1 wherein R is selected from the group consisting of hydrogen and alkyl of 1 to 5 carbon atoms and X is hydrogen.

4. A compound of claim 1 selected from the group consisting of 3-(1,2,5,6-tetrahydropyridin-3-yl)-phenol and its non-toxic, pharmaceutically acceptable acid addition salts.

5. A compound of claim 1 selected from the group consisting of 3-(1-propyl-1,2,5,6-tetrahydropyridin-3-yl)-phenol and its non-toxic, pharmaceutically acceptable acid addition salts.

6. A composition useful in treating Parkinson's disease and vomitting and nausea comprising an antiemetically and dopaminergic agonistically and/or antagonistically effective amount of at least one compound of claim 1 and its non-toxic, pharmaceutically acceptable acid addition salts and an inert pharmaceutical carrier.

7. A composition of claim 6 wherein R is selected from the group consisting of hydrogen, alkyl of 1 to 5 carbon atoms and aralkyl of 7 to 12 carbon atoms.

8. A composition of claim 6 wherein R is selected from the group consisting of hydrogen and alkyl of 1 to 5 carbon atoms and X is hydrogen.

9. A composition of claim 6 wherein the compound is selected from the group consisting of 3-(1,2,5,6-tetrahydropyridin-3-yl)-phenol and its non-toxic, pharmaceutically acceptable acid addition salts.

10. A composition of claim 6 wherein the compound is selected from the group consisting of 3-(1-propyl-1,2,5,6-tetrahydropyridin-3-yl)-phenol and its non-toxic, pharmaceutically acceptable acid addition salts.

11. A method of treating Parkinson's disease and vomitting and nausea in warm-blooded animals comprising administering to warm-blooded animals an antiemetically and dopaminergic agonistically and/or antagonistically effective amount of at least one compound of claim 1.

12. A method of claim 11 wherein R is selected from the group consisting of hydrogen, alkyl of 1 to 5 carbon atoms and aralkyl of 7 to 12 carbon atoms.

13. A method of claim 11 wherein R is selected from the group consisting of hydrogen and alkyl of 1 to 5 carbon atoms and X is hydrogen.

14. A method of claim 11 wherein the compound is selected from the group consisting of 3-(1,2,5,6-tetrahydropyridin-3-yl)-phenol and its non-toxic, pharmaceutically acceptable acid addition salts.

15. A method of claim 11 wherein the compound is selected from the group consisting of 3-(1-propyl-1,2,5,6-tetrahydropyridin-3-yl)-phenol and its non-toxic, pharmaceutically acceptable acid addition salts.

* * * * *